(12) United States Patent
Yasui et al.

(10) Patent No.: US 10,371,649 B2
(45) Date of Patent: Aug. 6, 2019

(54) RADIATION PHASE CHANGE DETECTION METHOD AND RADIATION IMAGING APPARATUS

(71) Applicant: CANON KABUSHIKI KAISHA, Tokyo (JP)

(72) Inventors: Nobuhiro Yasui, Yokohama (JP); Yoshihiro Ohashi, Tokyo (JP); Toru Den, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 280 days.

(21) Appl. No.: 15/491,161

(22) Filed: Apr. 19, 2017

(65) Prior Publication Data
US 2017/0315066 A1   Nov. 2, 2017

(30) Foreign Application Priority Data
Apr. 28, 2016   (JP) .................................. 2016-091055

(51) Int. Cl.
*G01N 23/04* (2018.01)
*G01N 23/20* (2018.01)
*G21K 1/06* (2006.01)

(52) U.S. Cl.
CPC ....... *G01N 23/04* (2013.01); *G01N 23/20075* (2013.01); *G21K 1/067* (2013.01); *G01N 2223/064* (2013.01); *G01N 2223/505* (2013.01); *G21K 2207/005* (2013.01)

(58) Field of Classification Search
CPC ............. G01N 23/04; G01N 23/20075; G01N 2223/064; G01N 2223/505; G21K 1/067; G21K 2207/005
See application file for complete search history.

(56) References Cited

U.S. PATENT DOCUMENTS 8,233,587 B2   7/2012   Sato et al.
2010/0260315 A1   10/2010   Sato et al.

FOREIGN PATENT DOCUMENTS

JP   2010-249533 A   11/2010
JP   4702455 B2   6/2011

*Primary Examiner* — Mark R Gaworecki
(74) *Attorney, Agent, or Firm* — Venable LLP (57) ABSTRACT

A radiation phase change detection method includes: arranging a two-dimensional optical image pickup element, which includes a scintillator, so that, when a period of a self-image generated through a phase grating is defined as $D_1$, and a pixel pitch of the two-dimensional optical image pickup element is defined as $D_2=kD_1$, k falls in a range of $1/2 < k \leq 3/2$, and so that interference fringes formed by $D_1$ and $D_2$ depending on a relationship in arrangement of the two-dimensional optical image pickup element with respect to the self-image have a period of 2 times $D_2$ or more and 100 times $D_2$ or less; acquiring images of the interference fringes before and after insertion of an object; and outputting an image on a phase change of the radiation caused by at least the object.

15 Claims, 5 Drawing Sheets

FIVE PIXELS

RADIATION PHASE CHANGE DETECTION METHOD AND RADIATION IMAGING APPARATUS

BACKGROUND OF THE INVENTION

Field of the Invention

The present invention relates to a method of imaging a phase change of a radiation and a radiation imaging apparatus thereuse.

Description of the Related Art

As opposed to a related-art method of imaging an absorption contrast of a radiation, in particular, an X-ray, a method of imaging a phase change has been attracting attention for its excellent property of rendering a light element, that is, a soft tissue of a living body and the like.

In particular, among others, a method in which an X-ray Talbot-Lau interferometer is used has been researched and developed for practical use because a general X-ray source used in medical settings and laboratories may be used therein. In a related-art Talbot-Lau interferometer, an absorption grating is arranged at an image forming position of a self-image that is an interference pattern based on the Talbot effect, which is formed by a phase grating and has a period of several micrometers, and Moire fringes, which are generated as a result and form a pattern having a period that is larger than that of the self-image, are imaged by a two-dimensional radiation detector. The reason why the Moire fringes are imaged in the method using the X-ray Talbot-Lau interferometer as described above is that there is no detector capable of directly resolving the self-image. Moreover, the absorption grating is produced by a semiconductor process with silicon and the like, and gold plating and the like, and hence is very expensive. To address this problem, in Japanese Patent No. 4702455, there is disclosed a unit configured to form Moire fringes using, instead of an absorption grating that acts on an X-ray, an optical diffraction grating that acts on visible light, which is obtained by converting the X-ray once by a scintillator. This unit has an advantage of eliminating the need for an absorption grating, which uses gold and is expensive, and a feature that the two-dimensional radiation detector may be formed of the following three components: a scintillator, an optical diffraction grating, and an image pickup element.

However, also in the above-mentioned two-dimensional radiation detector, the two-dimensional radiation detector is formed of the three components: the scintillator, the optical diffraction grating, and the image pickup element, and hence there has been a need to separately produce the optical diffraction grating in addition to the scintillator and the image pickup element.

SUMMARY OF THE INVENTION

According to one embodiment of the present invention, there is provided a radiation phase change detection method for detecting a phase change of a radiation, the radiation phase change detection method including changing an interference state of the radiation using a phase grating configured to cause interference in the radiation radiated by a radiation source, a scintillator configured to convert the radiation into light, and an image pickup element including two-dimensionally arranged pixels (hereinafter also referred to as "two-dimensional optical image pickup element"), in which as the image pickup element, an element is used which is incapable of sampling a period of a self-image of the radiation generated through the phase grating, and is capable of sampling interference fringes generated between the period of the self-image and a period of a pixel pitch of the two-dimensional optical image pickup element.

According to one embodiment of the present invention, there is provided a radiation phase change detection method for detecting a phase change of a radiation, the radiation phase change detection method including: arranging a two-dimensional optical image pickup element, which includes a scintillator, so that, when a period of a self-image generated through a phase grating is defined as $D_1$, and a pixel pitch of the two-dimensional optical image pickup element is defined as $D_2=k*D_1$, k falls in a range of $1/2<k\leq3/2$, and so that interference fringes formed by $D_1$ and $D_2$ depending on a relationship in arrangement of the two-dimensional optical image pickup element with respect to the self-image have a period of 2 times $D_2$ or more and 100 times $D_2$ or less; acquiring a phase change of the interference fringes before and after insertion of an object; and outputting an image on a phase change of the radiation caused by at least the insertion of the object.

Further, according to one embodiment of the present invention, there is provided a radiation imaging apparatus, which is a radiation imaging apparatus utilizing the above-mentioned radiation phase change detection method.

According to the radiation phase change detection method of the present invention, interference fringes can be generated and a phase change of the interference fringes can be detected with the structure including only the scintillator and the image pickup element without the need for an absorption grating or an optical diffraction grating, which has been required in the related-art method.

Further features of the present invention will become apparent from the following description of exemplary embodiments with reference to the attached drawings.

DESCRIPTION OF THE EMBODIMENTS

Now, modes for embodying the present invention are described with reference to the drawings.

Description of the Structure According to the Present Invention

Figure 1:
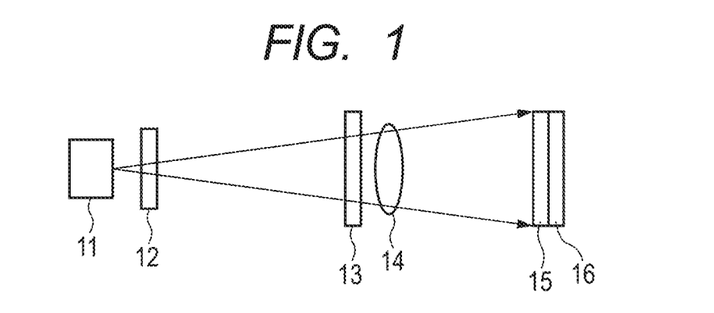
FIG. 1 is a diagram for illustrating the structure of a radiation imaging apparatus according to the present invention.

In FIG. 1, an example of the structure of a radiation imaging apparatus based on a radiation phase change detection method according to the present invention is illustrated taking, as an example, a case of using an X-ray as a radiation.

The radiation imaging apparatus according to the present invention includes, as main components, an X-ray source 11, a source grating 12, a phase grating 13, a scintillator 15, and a two-dimensional optical image pickup element 16.

As the X-ray source 11, tubes of different target materials may be selected in consideration of characteristics of an object 14 and the like. Examples of the target material include Cu, Ag, Mo, and W. When a general X-ray source 11 having a large focal point size is used, the source grating 12 may be inserted to adjust a size of a radiation source. As the source grating 12, such source grating 12 as described in Japanese Patent Application Laid-Open No. 2010-249533 may be used. Moreover, the phase grating 13, which may be produced through a semiconductor process and is made of Si or the like, plays a role of causing interference between spherical waves diffracted by respective slits of the phase grating 13 to form a self-image at a point corresponding to the Talbot length downstream of a grating surface. In the radiation phase change detection method according to the present invention, how the self-image is changed with a change in interference state of the radiation before and after insertion of the object 14 is captured to detect a phase change of the self-image. The object 14 may be inserted between the phase grating 13 and the X-ray source 11 or the source grating 12, or between the phase grating 13 and the scintillator 15.

Figure 2A:
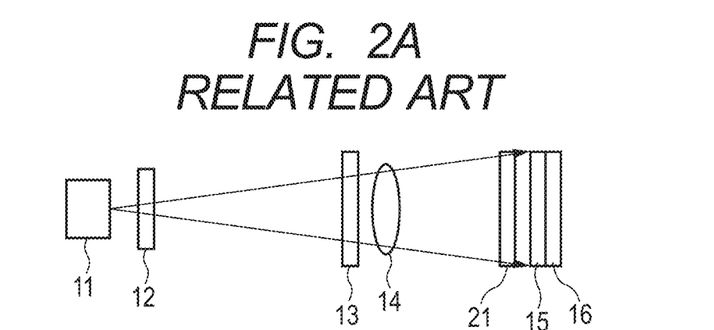
FIG. 2A and FIG. 2B are each a diagram for illustrating the structure of a radiation imaging apparatus according to the related art.
Figure 2B:
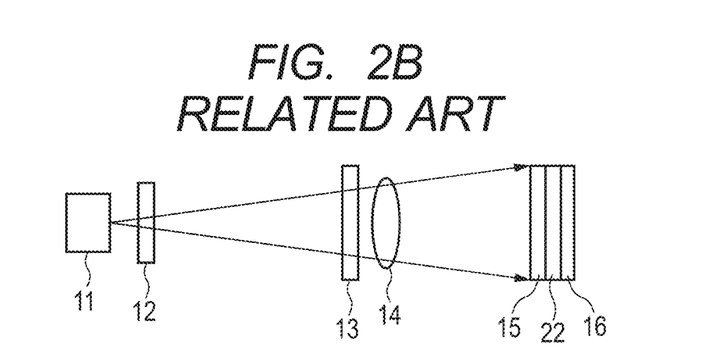

In each of FIG. 2A and FIG. 2B, there is illustrated an example of the structure of a radiation imaging apparatus based on a radiation phase change detection method according to the related art. Also in the radiation phase change detection method according to the related art, as in the radiation phase change detection method according to the present invention, a change of the self-image caused by insertion of the object 14 is captured to detect the phase change of the self-image. The radiation imaging apparatus in each of FIG. 2A and FIG. 2B includes an X-ray source 11, a source grating 12, a phase grating 13, a scintillator 15, a two-dimensional optical image pickup element 16, and an absorption grating 21 (FIG. 2A) or an optical diffraction grating 22 (FIG. 2B). As with the phase grating 13, the absorption grating 21 is a grating for the X-ray having a very high aspect ratio, which is formed by producing a mold made of Si or the like through the semiconductor process, and further being implanted through, for example, plating using an element having a high atomic number, for example, gold. In particular, having a periodicity of 10 μm or less and requiring a thickness of 100 μm or more, the absorption grating 21 is a very expensive part in consideration of a process cost and a cost of materials.

In the radiation phase change detection method according to the related art, the self-image having a period of 10 μm or less cannot be directly resolved. Therefore, as illustrated in FIG. 2A, there is adopted a method in which interference fringes of the X-ray, which have a period that is larger than those formed by the self-image and the absorption grating 21, are converted into visible light by the scintillator 15, and are imaged by the two-dimensional optical image pickup element 16. Moreover, in consideration of responsiveness for sufficiently absorbing the X-ray and radiating a large amount of scintillation light, the scintillator 15 needs to have a thickness of at least 150 μm or more depending on energy of the X-ray.

Moreover, in FIG. 2B, there is illustrated a radiation phase change detection method in which, instead of the absorption grating 21 for the X-ray, the self-image of the X-ray is converted into the visible light by the scintillator 15, and then the interference fringes are generated with the optical diffraction grating 22. In the radiation phase change detection method illustrated in FIG. 2B, a scintillator 15 having a very high definition is required. Therefore, the scintillator 15 needs to have a very small thickness, and it is assumed that the radiation phase change detection method illustrated in FIG. 2B has significantly reduced detection sensitivity as compared to the radiation phase change detection method illustrated in FIG. 2A. Moreover, it is also required to produce the optical diffraction grating 22, although there is no need to use gold.

In contrast, in the radiation phase change detection method according to the present invention, the absorption grating 21 or the optical diffraction grating 22 is not required. The reasons are as follows.

The first reason is that a scintillator 15 capable of resolving 100 lp/mm (lp: line pair) at least with a thickness of 150 μm is used. The expression "100 lp/mm" means that it is spacial frequency with 100 light and dark lines per mm, and the scintillator 15 has a very high resolution which enables discrimination of light having a periodicity of 10 μm or less.

The second reason is that a light receiving portion of the two-dimensional optical image pickup element 16 has a predetermined pixel pitch, and is capable of causing interference with the self-image. Therefore, the interference fringes may be generated, and desired imaging may be performed without inserting the optical diffraction grating 22 as in the radiation phase change detection method illustrated in FIG. 2B. In other words, the two-dimensional optical image pickup element 16 is incapable of sampling the period of the self-image of the radiation generated through the phase grating 13, but is capable of sampling the interference fringes generated through the phase grating 13. In the present invention, it is preferred that the above-mentioned interference be Moire interference, and that the above-mentioned interference fringes be Moire fringes.

For the two reasons described above, in the radiation phase change detection method according to the present invention, when it is defined that $D_2 = k*D_1$, where $D_1$ represents a period of the self-image formed by the phase grating 13, and $D_2$ represents the pixel pitch of the two-dimensional optical image pickup element 16, and when k falls in a range of $1/2 < k \leq 3/2$, interference can be caused between the self-image and the light receiving portion of the two-dimensional optical image pickup element 16. Moreover, it is preferred that a relationship in arrangement of the two-dimensional optical image pickup element 16 with respect to the self-image be adjusted so that the interference fringes have a period of 2 times the pixel pitch $D_2$ or more and 100 times the pixel pitch $D_2$ or less. An example of the adjustment of the relationship in arrangement of the two-dimensional optical image pickup element 16 with respect to the self-image may include adjustment of a rotation angle of the two-dimensional optical image pickup element 16 with respect to the self-image. When the period of the interference fringes is larger than 100 times the pixel pitch $D_2$, the resolution of the obtained image becomes much lower with respect to the pixel pitch $D_2$, and the two-dimensional optical image pickup element 16 has an unnecessarily high resolution with respect to the period of the interference fringes. In this case, the phase change of the radiation caused by the object 14 may be detected with the radiation phase change detection method according to the present invention, but the number of light beams that enter each pixel of the two-dimensional optical image pickup element 16 is significantly reduced, and may cause statistical noise. Therefore, it is preferred to adjust the rotation angle of the two-dimensional optical image pickup element 16 so that the interference fringes have the period of 2 times the pixel pitch $D_2$ or more and 100 times the pixel pitch $D_2$ or less. It is more preferred that the interference fringes have a period of 2 times the pixel pitch $D_2$ or more and 20 times the pixel pitch $D_2$ or less, and it is further preferred that the interference fringes have a period in the vicinity of 4 times the pixel pitch $D_2$.

As shown in Table 1, a relationship between the period of the interference fringes when the self-image has a period of 8 μm and the pixel pitch $D_2$ was calculated with Expression 1. When the pixel pitch $D_2$ has a value close to the period $D_1$ of the self-image, the period of the interference fringes is significantly increased. In this case, as calculated with Expression 2, a rotation angle θ of the two-dimensional optical image pickup element 16 may be adjusted to adjust the interference fringes to have the period of 2 times the pixel pitch $D_2$ or more and 100 times the pixel pitch $D_2$ or less (Table 1). For example, when the self-image has a period of 8 μm, and a pixel pitch is 8.01 μm, the rotation angle θ of the two-dimensional optical image pickup element 16 may be rotated by 12° to adjust the period of the interference fringes from 800 times the pixel pitch $D_2$ to 4.78 times the pixel pitch $D_2$. The two-dimensional optical image pickup element 16 may be rotated clockwise or counterclockwise, and the rotation angle may be adjusted arbitrarily so that the interference fringes have the period of 2 times the pixel pitch $D_2$ or more and 100 times the pixel pitch $D_2$ or less. Further, the two-dimensional optical image pickup element 16 may be adjusted by being translated.

$$\text{Period of interference fringes} = D_1 \times D_2 / |D_1 - D_2| \quad (1)$$

$$\text{Period of interference fringes} = D = \{(1/D_1) + (1/D_2) - ((2/D_1 * D_2) * \cos\theta)\}^{\wedge}(-\tfrac{1}{2}) \quad (2)$$

TABLE 1

| Period $D_1$ of Self-image [μm] | Pixel Pitch $D_2$ [μm] | Period of Interference Fringes/Pixel Pitch $D_2$ | |
|---|---|---|---|
| | | Without Adjustment | Rotated by 12° |
| 8.00 | 12.00 | 2.00 | — |
| 8.00 | 10.00 | 4.00 | 2.92 |
| 8.00 | 9.00 | 8.00 | 3.93 |
| 8.00 | 8.01 | 800.00 | 4.78 |
| 8.00 | 7.00 | 8.00 | 4.31 |
| 8.00 | 6.00 | 4.00 | 3.24 |
| 8.00 | 4.01 | 2.01 | — |

In the relationship: $D_2 = k*D_1$ in the radiation phase change detection method according to the present invention, when k is ½ or less ($k \leq \tfrac{1}{2}$), the period of the self-image may be directly measured instead of the period of the interference fringes based on the sampling theorem. The radiation phase change detection method according to the present invention provides an advantage that an element having a larger pixel pitch $D_2$ may be used by forming the interference fringes. For example, in an optical image pickup element (e.g., CCD or CMOS image sensor) having a relatively large area, when the pixel pitch $D_2$ is small, a pixel number is increased, and there are problems in that reading takes time, and in that yield of the sensor itself is affected. Therefore, in the radiation phase change detection method according to the present invention, the pixel pitch $D_2$ is set as large as possible in a desired range of image resolutions to have an effect that the above-mentioned problems can be solved. For example, in the radiation phase change detection method according to the present invention, when the period of the self-image is 10 μm, a two-dimensional optical image pickup element 16 including pixels having a pixel pitch $D_2$ of 5 μm or more may be used.

Meanwhile, when the pixel pitch $D_2$ does not satisfy $k \leq 3/2$, a ratio of the pixel pitch $D_2$ to the period of the interference fringes becomes smaller than 2 times, and the interference fringes themselves cannot be sampled. Therefore, in the radiation phase change detection method according to the present invention, when the period of the self-image is 10 μm, a two-dimensional optical image pickup element 16 including pixels having a pixel pitch $D_2$ of 15 μm or less may be used.

In the above description, there has been described the example in which the X-ray is used as the radiation, but any radiation may be used as long as the radiation may excite and cause the scintillator 15 to emit light. Examples of such radiation include a γ-ray and a neutron ray.

Moreover, a two-dimensional optical image pickup element 16 having any aperture ratio in one pixel, that is, any ratio between an area of a light receiving portion 32 and an area of a pixel may be used, but the aperture ratio is reflected on a contrast of fringes obtained when the interference fringes are imaged.

Figure 3:
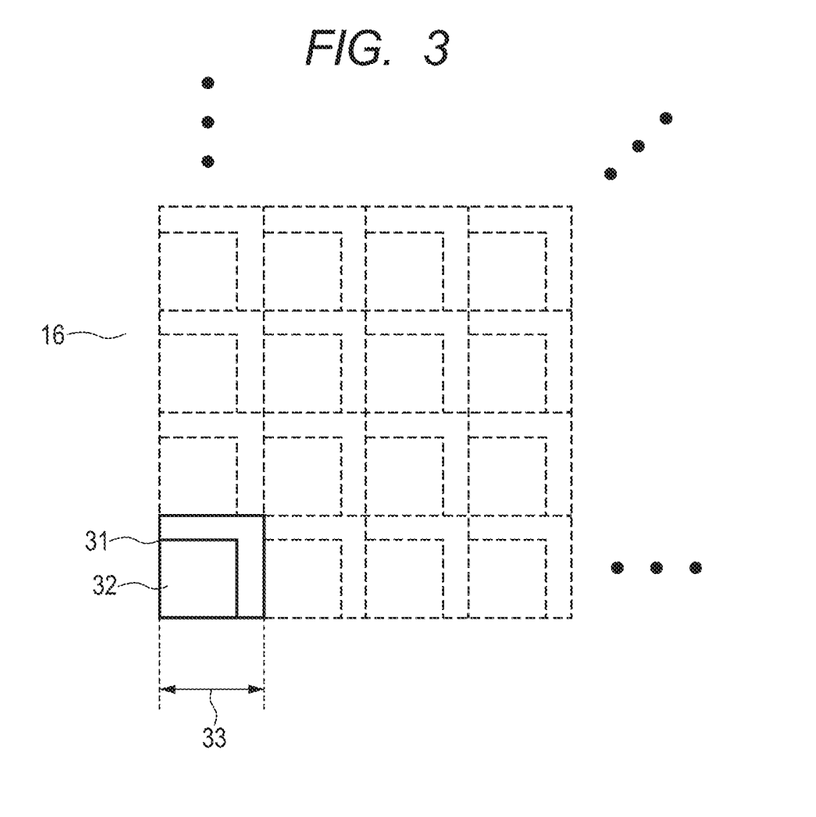
FIG. 3 is an enlarged view of a two-dimensional optical image pickup element.
Figure 4A:
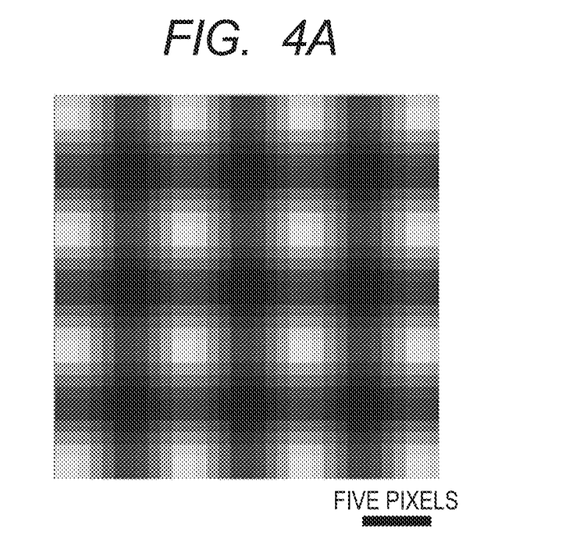
FIG. 4A is a view of an image of interference fringes obtained with a radiation phase change detection method according to the present invention.
Figure 4B:
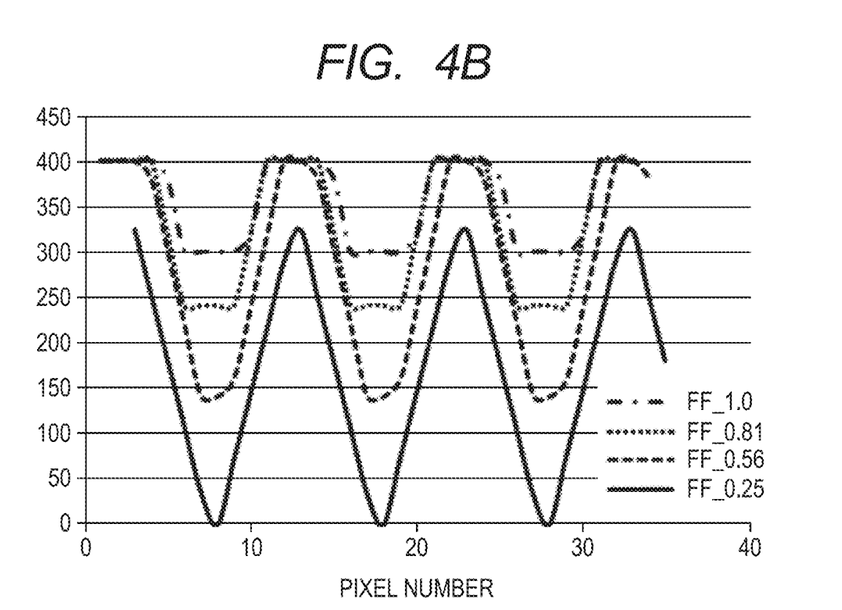
FIG. 4B is a graph for showing dependency of a contrast of the interference fringes on an aperture ratio.

In FIG. 3, the two-dimensional optical image pickup element 16 having a pixel pitch 33 is illustrated. When an aperture ratio (fill factor: FF) expressed by P/S, where S represents an area of a pixel 31 of the two-dimensional optical image pickup element 16, and P represents an area of the light receiving portion 32 in the pixel 31, falls in a range of from 0.01 to 1.0, a satisfactory contrast of the interference fringes may be obtained. For example, when the self-image had a period of 8 μm, and the pixel pitch 33 of the two-dimensional optical image pickup element 16 was 7.2 μm, the aperture ratio was changed to obtain images. When the aperture ratio was 0.56, an image of the interference fringes shown in FIG. 4A was obtained, and when the aperture ratio was changed, a cross-sectional profile of the image was changed as shown in FIG. 4B. As shown in FIG. 4B, an amplitude (contrast) of the interference fringes is changed with the change in aperture ratio, but the periodicity is not impaired. Therefore, a wide range of aperture ratios may be selected.

In the radiation phase change detection method according to the present invention, a phase change in a result obtained by imaging the interference fringes generated between the self-image and the two-dimensional optical image pickup element 16, which is caused by presence or absence of the object 14, is analyzed. An analysis method may be any method, and it is preferred that a method of analyzing the phase change be a Fourier transform method. The Fourier transform method may be used to analyze the phase change at a resolution corresponding to a period of the obtained interference fringes. Moreover, the phase change may be analyzed by fringe scanning interferometry, with which a high resolution may be obtained although a plurality of imaging operations are required.

In the radiation phase change detection method according to the present invention, the phase change of the interference fringes generated between the self-image and the two-dimensional optical image pickup element 16 by the insertion of the object 14 may be acquired as an image through the above-mentioned analysis. Therefore, in the radiation phase change detection method according to the present invention, the phase change of the radiation caused by the insertion of the object 14 may be detected by comparing an image of the interference fringes obtained when the object 14 is not inserted and an image of the interference fringes obtained when the object 14 is inserted with each other to output a distortion in the interference fringes due to a change in period D1 of the self-image, which is caused by the phase change of the radiation, as an image.

[Eutectic Phase-Separated Scintillator]

Figure 5:
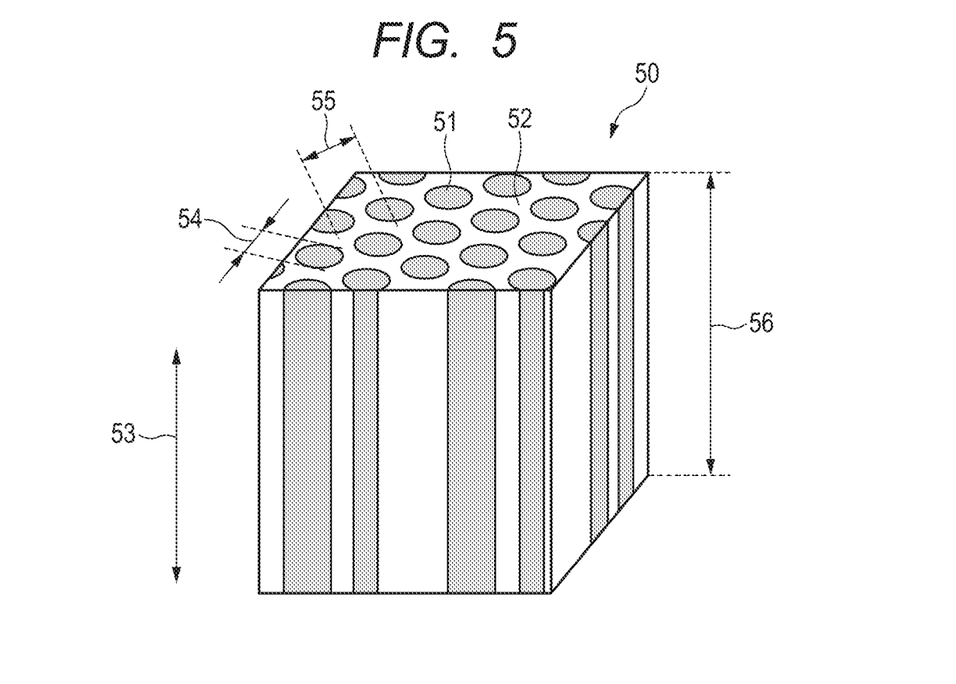
FIG. 5 is a view for illustrating a eutectic phase-separated scintillator.

In FIG. 5, an example of the scintillator 15 used in the radiation phase change detection method according to the present invention is illustrated.

It is preferred that the scintillator 15 used in the radiation phase change detection method according to the present invention be an uniaxial eutectic phase-separated scintillator 50, which includes a plurality of first phases 51, which serves as a scintillator, and a second phase 52, has uniaxiality in a direction connecting two surfaces (hereinafter sometimes referred to as "first surface" and "second surface") that are not on the same plane, and has a light guiding property in that direction. The plurality of first phases 51 are phases having columnar fiber structures surrounded by the second phase 52 and each having a unidirectional property along an optical waveguide direction 53, and exist at a certain average structural period 55 in the second phase 52.

It is preferred that the first surface and the second surface be substantially perpendicular (within ±20°) to the direction (optical waveguide direction 53) along which the first phases 51 extend.

Moreover, the first phases 51 need to be phases having a high refractive index, and the second phase 52 needs to be a phase having a low refractive index. Further, the first phases 51 serve as a scintillator, and hence the first phases 51 are capable of being excited by absorbing the radiation, and of guiding emitted light as with an optical fiber.

As materials of the first phases 51 and the second phase 52 of such eutectic phase-separated scintillator 50, a material system of such combination as shown in Table 2 may be used.

TABLE 2

| Material of First Phases 51 | Material of Second Phase 52 |
|---|---|
| $GdAlO_3$ | $Al_2O_3$ |
| CsI | $NaNO_3$ |
| ZnO | $ZnF_2$ |

A shape of the first phase 51 is not limited to the cylindrical shape as illustrated in FIG. 5, but may be a columnar body having an elliptical cross section, a columnar body having a side surface that is formed of an arbitrary curved surface, or a columnar body formed of a plurality of surfaces and having a polygonal cross section. It is preferred that a diameter 54 of a column of the first phase 51 be 50 nm or more and 30 μm or less. In other words, when the first phase 51 has a circular cross section, it is preferred that a diameter of the circular cross section be 50 nm or more and 30 μm or less. Moreover, when the first phase 51 has an elliptical cross section, it is preferred that a major axis and a minor axis of the elliptical cross section be 50 nm or more and 30 μm or less. Further, when the first phase 51 has a polygonal cross section, it is preferred that, of values that are twice distances between a center of gravity and vertices, the smallest value and the largest value be 50 nm or more and 30 μm or less.

Moreover, it is preferred that the average structural period 55 of the first phases 51 in the eutectic phase-separated scintillator 50, which is expressed by an average distance between centers of gravity of cross sections of the first phases 51, be 500 nm or more and 50 μm or less. It should be noted, however, that the average structural period 55 needs to be smaller than half the period $D_1$ of the self-image.

The first phases 51 may have an interruption, a branch, coupling, and the like, but it is preferred that the first phases 51 be continuous between the first surface and the second surface.

A thickness 56 of the eutectic phase-separated scintillator 50 may be selected as appropriate depending on energy of the absorbed radiation so that the first phases 51 serve as a scintillator. It is preferred that the thickness 56 of the eutectic phase-separated scintillator 50 for use in the radiation phase change detection method according to the present invention be 10 μm or more and 40 mm or less, and it is more preferred that the thickness 56 be 50 μm or more and 5 mm or less.

Figure 6:
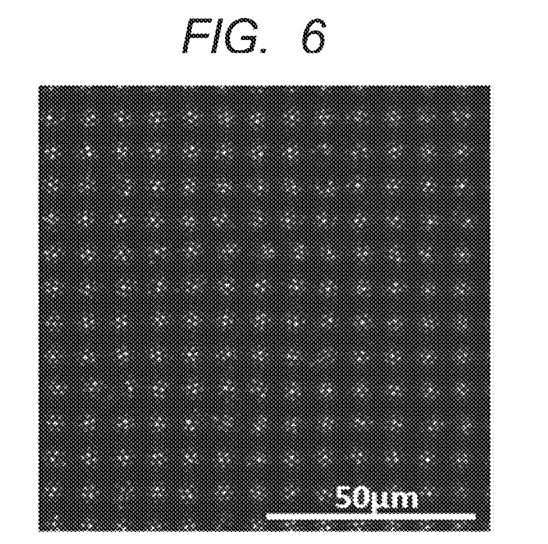
FIG. 6 is a view of an image for showing a waveguide state of a periodic pattern of the eutectic phase-separated scintillator.

The eutectic phase-separated scintillator 50 having such structure has performance capable of sufficiently resolving the period $D_1$ of the self-image, which is 8 μm, when the average structural period 55 is 1.68 μm, the first phase 51 is $GdAlO_3$ having columns of an average diameter 54 of 1.24 μm, and the thickness 56 of the eutectic phase-separated scintillator 50 is 150 μm, for example. In FIG. 6, there is shown a transmission image obtained by allowing a visible radiation simulating a self-image having a period of 8 μm to enter from the rear surface to be transmitted by the above-mentioned eutectic phase-separated scintillator 50. As can be seen from FIG. 6, even the self-image of 10 μm or less is transmitted by each of the first phases 51.

Therefore, information on the self-image is not significantly modulated or a diffraction phenomenon is not caused, and hence the self-image is not degraded, due to the structure of the eutectic phase-separated scintillator 50. Therefore, when the period $D_1$ of the self-image and $D_2$, which is the pixel pitch 33 of the two-dimensional optical image pickup element 16, satisfy the relationship in the radiation phase change detection method according to the present invention, it is possible to provide a radiation phase change detection method, which eliminates the need for the absorption grating 21 or the optical diffraction grating 22 for generating the interference fringes.

In the radiation phase change detection method according to the present invention, it is preferred to adopt an arrangement in which the first phases 51 of the eutectic phase-separated scintillator 50 are brought into direct contact with an image pickup surface of the two-dimensional optical image pickup element 16. In this case, the first phases 51 may be bonded to the image pickup surface of the two-dimensional optical image pickup element 16. The two-dimensional optical image pickup element 16 may be a special element, or a general element in which a microlens is provided for each pixel. Moreover, even in the case of direct bonding, there is no need to bring a light receiving surface and the scintillator 15 into direct contact with each other, and various protective layers may be interposed.

Further, in order to take measures to reduce spot noise generated by the radiation that has been transmitted through the first phases 51 of the eutectic phase-separated scintillator 50 entering the two-dimensional optical image pickup element 16, it is preferred to insert, between the eutectic phase-separated scintillator 50 and the two-dimensional optical image pickup element 16, a fiber optic plate (hereinafter also referred to as "FOP") having a periodicity that is half the period of the self-image or less and no effect on a periodic component of interest.

[Radiation Phase Change Detection Apparatus]

The radiation imaging apparatus according to the present invention includes a radiation source, a phase grating 13, a scintillator 15, and a two-dimensional optical image pickup element 16.

In the phase change detection method according to the present invention, the need for the absorption grating 21 or the optical diffraction grating 22 is eliminated, and hence there is no need to provide such component in the radiation imaging apparatus according to the present invention. The radiation imaging apparatus according to the present invention may also include a driving system configured to adjust a position of each part and insert the object 14, an arithmetic section configured to extract and analyze a phase change, and an image acquisition unit configured to visualize the phase change. When the X-ray is used as the radiation, the radiation imaging apparatus may be formed using the X-ray source 11, the phase grating 13, the scintillator 15, and the two-dimensional optical image pickup element 16, which have been described above as components of the radiation phase change detection method according to the present invention. In this case, an apparatus length of the radiation imaging apparatus may be 2 m or less.

Example 1

Using a eutectic phase-separated scintillator 50 in which the material of the first phases 51 is $GdAlO_3$ and the material of the second phase 52 is $Al_2O_3$, an examination was performed on whether or not the information on the self-image was significantly modulated by the eutectic phase-separated scintillator 50. The above-mentioned eutectic phase-separated scintillator 50 is a eutectic phase-separated scintillator 50 that is obtained by adding Tb to Gd sites and emits green light, for which the two-dimensional optical image pickup element 16 has high receiving sensitivity. Moreover, the above-mentioned eutectic phase-separated scintillator 50 has a thickness 56 of 150 µm and an average structural period 55 of 1.68 µm, and includes the first phases 51 having columns of an average diameter 54 of 1.24 µm.

As an X-ray optical system, the X-ray source 11 containing tungsten as a target and having radiation quality of 28 keV with a 1-mm Al filter was used with an insertion of the source grating 12 having a pitch of 12.75 µm. A period $D_1$ of the self-image formed by a two-dimensional phase grating 13 made of silicon was 8.24 µm.

Under the above-mentioned conditions, the eutectic phase-separated scintillator 50 was arranged at a position at which the self-image was formed, and the self-image was directly taken for about 40 seconds while being enlarged by a lens. At this time, a distance from the source grating 12 to the eutectic phase-separated scintillator 50 is 1,185 mm, and a resolution per pixel in a lens optical system is 0.65 µm.

Figure 7:
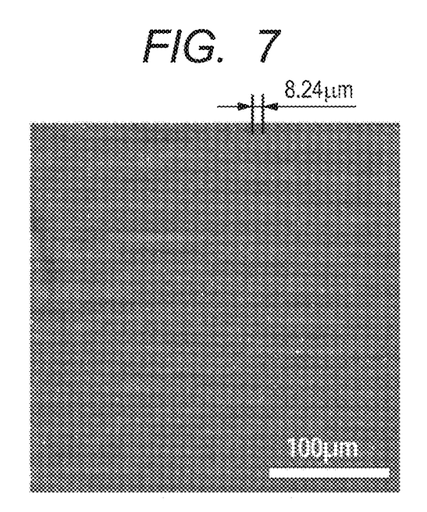
FIG. 7 is a view of a self-image taken by the eutectic phase-separated scintillator.

A self-image of an exit surface of the eutectic phase-separated scintillator 50 taken under the above-mentioned conditions is shown in FIG. 7. In FIG. 7, the self-image having a period of 8.24 µm was clearly rendered. As a result, it was able to be confirmed that a periodic pattern of the self-image was not modulated by the eutectic phase-separated scintillator 50.

Further, an image was taken by changing the thickness 56 of the eutectic phase-separated scintillator 50 to 300 µm and bonding the eutectic phase-separated scintillator 50 to a CCD having $D_2$, which is the pixel pitch 33, of 4.4 µm (k=0.534 based on the expression: $D_2=k*D_1$ in the radiation phase change detection method according to the present invention). Then, the period $D_1$ of 8.24 µm of the self-image was detected as interference fringes (Moire fringes) having a period of about 9.4 µm. Moreover, a change in Moire fringes before and after insertion of a nylon ball having a diameter of 4 mm, which was used as the object 14, was able to be extracted and analyzed as modulation of the frequency component of interest with the Fourier transform method.

As described above, it was confirmed that the radiation phase change detection method according to the present invention is effective as a method of detecting the phase change in the period of the interference fringes caused by the interference between the self-image, which is formed by the radiation and the phase grating 13, and the two-dimensional optical image pickup element 16 without degrading the self-image by the scintillator.

Example 2

Figure 8A:
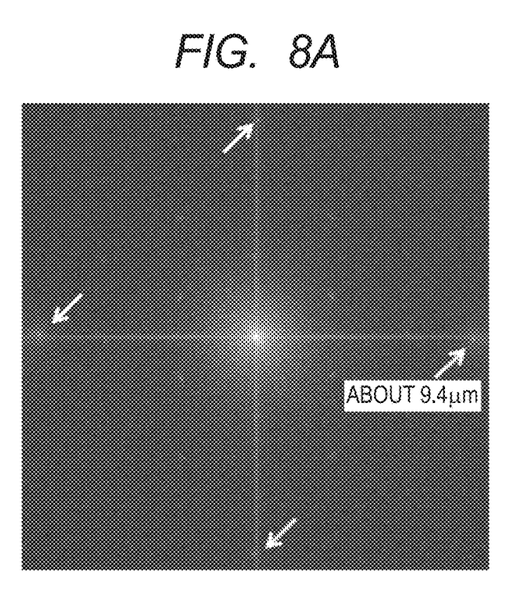
FIG. 8A is a view of a Fourier transform image reflecting a period of Moire fringes.

An image of the interference fringes was taken as in Example 1 except that the thickness 56 of the eutectic phase-separated scintillator 50 in Example 1 was changed to 250 Tim, that an FOP having a thickness of about 2.5 mm and a periodicity of about 3 µm was inserted between the eutectic phase-separated scintillator 50 and the two-dimensional optical image pickup element 16, and that imaging time was changed to 8 seconds. As a result of performing analysis with the Fourier transform method, as shown in FIG. 8A, the period $D_1$ of the self-image was detected as interference fringes (Moire fringes) having a period of about 9.4 µm though with diffraction spots having a long period caused by the FOP.

Figure 8B:
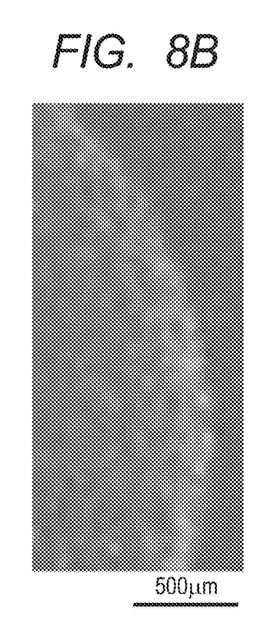
FIG. 8B is a view of a phase retrieval image generated by a Fourier transform method reflecting the period of the Moire fringes.

In addition, a phase change before and after insertion of a nylon ball having a diameter of 4 mm was extracted and analyzed with the Fourier transform method. As a result, an image of FIG. 8B was obtained, and it was able to be confirmed that, in the radiation phase change detection method according to the present invention, the insertion of the FOP having a periodicity of half the period $D_1$ of the self-image or less did not have a problematic effect on the periodic component of the period $D_1$ of the self-image in the radiation phase change detection method according to the present invention, and had the effect of reducing spot noise.

With the radiation phase change detection method according to the present invention, the need for the absorption grating or the optical diffraction grating is eliminated, and hence the radiation phase change detection apparatus can be formed in a compact size. The radiation phase change detection method according to the present invention is applicable to the X-ray, the γ-ray, and the neutron ray. In particular, in an X-ray region, the radiation phase change detection method can be used for phase change imaging apparatuses for medical and industrial purposes.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-091055, filed Apr. 28, 2016, which is hereby incorporated by reference herein in its entirety.

What is claimed is:

1. A radiation phase change detection method for detecting a phase change of a radiation, the radiation phase change detection method comprising changing an interference state of the radiation using a phase grating configured to cause interference in the radiation radiated by a radiation source, a scintillator configured to convert the radiation into light, and a two-dimensional optical image pickup element,
   wherein the two-dimensional optical image pickup element is incapable of sampling a period of a self-image of the radiation generated through the phase grating, and is capable of sampling interference fringes generated between the period of the self-image and a period of a pixel pitch of the two-dimensional optical image pickup element.

2. A radiation phase change detection method according to claim 1, further comprising placing an object between the radiation source and the phase grating, or between the phase grating and the scintillator.

3. A radiation phase change detection method according to claim 1, further comprising arranging the two-dimensional optical image pickup element so that, when the period of the self-image is defined as $D_1$, and the pixel pitch of the two-dimensional optical image pickup element is defined as $D_2=k*D_1$, k falls in a range of $½<k≤3/2$.

4. A radiation phase change detection method according to claim 3, further comprising arranging the two-dimensional optical image pickup element so that the interference fringes formed by $D_1$ and $D_2$ have a period of 2 times $D_2$ or more and 100 times $D_2$ or less.

5. A radiation phase change detection method for detecting a phase change of a radiation, the radiation phase change detection method comprising:
   arranging a two-dimensional optical image pickup element, which includes a scintillator, so that, when a period of a self-image generated through a phase grating is defined as $D_1$, and a pixel pitch of the two-dimensional optical image pickup element is defined as $D_2=k*D_1$, k falls in a range of $½<k≤3/2$, and so that interference fringes formed by $D_1$ and $D_2$ depending on a relationship in arrangement of the two-dimensional optical image pickup element with respect to the self-image have a period of 2 times $D_2$ or more and 100 times $D_2$ or less;
   acquiring a phase change of the interference fringes before and after insertion of an object; and
   outputting an image on a phase change of the radiation caused by at least the insertion of the object.

6. A radiation phase change detection method according to claim 5, further comprising adjusting the relationship in arrangement of the two-dimensional optical image pickup element with respect to the self-image through rotation so that the interference fringes have a period of 100 times $D_2$ or less.

7. A radiation phase change detection method according to claim 5, wherein the scintillator comprises a scintillator capable of resolving 100 lp/mm at least with a thickness of 150 μm.

8. A radiation phase change detection method according to claim 5, wherein the scintillator comprises a eutectic phase-separated scintillator, in which a plurality of fiber structures containing $GdAlO_3$ are surrounded by a material containing $Al_2O_3$.

9. A radiation phase change detection method according to claim 5, further comprising arranging a fiber optic plate, which has a periodicity of half the period $D_1$ of the self-image or less, between the scintillator and the two-dimensional optical image pickup element.

10. A radiation imaging apparatus, comprising:
    a radiation source;
    a phase grating configured to cause interference in a radiation radiated by the radiation source;
    a scintillator configured to convert the radiation into light; and
    a two-dimensional optical image pickup element,
    wherein the two-dimensional optical image pickup element is incapable of sampling a period of a self-image of the radiation generated through the phase grating, and is capable of sampling interference fringes generated between the period of the self-image and a period of a pixel pitch of the two-dimensional optical image pickup element.

11. A radiation imaging apparatus according to claim 10, wherein the two-dimensional optical image pickup element is arranged so that, when the period of the self-image is defined as $D_1$, and the pixel pitch of the two-dimensional optical image pickup element is defined as $D_2=k*D_1$, k falls in a range of $½<k≤3/2$.

12. A radiation imaging apparatus according to claim 10, wherein the two-dimensional optical image pickup element is arranged so that the interference fringes formed by $D_1$ and $D_2$ have a period of 2 times $D_2$ or more and 100 times $D_2$ or less.

13. A radiation imaging apparatus, comprising:
    a radiation source;
    a phase grating;
    a scintillator; and
    a two-dimensional optical image pickup element,
    wherein the radiation imaging apparatus is configured to detect a phase change of a radiation by:
      arranging the two-dimensional optical image pickup element so that, when a period of a self-image generated through the phase grating is defined as $D_1$, and a pixel pitch of the two-dimensional optical image pickup element, which includes the scintillator, is defined as $D_2=k*D_1$, k falls in a range of $½<k≤3/2$, and so that interference fringes formed depending on a relationship in arrangement of the two-dimensional optical image pickup element with respect to the self-image have a period of 2 times $D_2$ or more and 100 times $D_2$ or less;
      acquiring a phase change of the interference fringes before and after insertion of an object; and
      outputting an image on a phase change of the radiation caused by at least the object.

14. A radiation imaging apparatus according to claim 13, wherein the radiation source comprises an X-ray source.

15. A radiation imaging apparatus according to claim 13, further comprising at least one selected from the group consisting of a driving system, an arithmetic section, and an image acquisition unit.

* * * * *